United States Patent
Jeon et al.

(10) Patent No.: US 10,413,884 B2
(45) Date of Patent: Sep. 17, 2019

(54) CATALYTIC CRACKING CATALYST FOR RFCC PROCESS WITH MAXIMIZED DIESEL YIELDS AND A METHOD FOR THE PREPARATION THEREOF

(71) Applicant: SK Innovation Co., Ltd., Seoul (KR)

(72) Inventors: Hee-Jung Jeon, Daejeon (KR); Yong-Woo Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 221 days.

(21) Appl. No.: 14/721,260

(22) Filed: May 26, 2015

(65) Prior Publication Data

US 2015/0336084 A1    Nov. 26, 2015

(30) Foreign Application Priority Data

May 23, 2014  (KR) .................. 10-2014-0062083

(51) Int. Cl.

| | |
|---|---|
| *B01J 21/16* | (2006.01) |
| *B01J 37/04* | (2006.01) |
| *B01J 37/08* | (2006.01) |
| *C07C 5/333* | (2006.01) |
| *B01J 21/18* | (2006.01) |
| *B01J 23/78* | (2006.01) |
| *B01J 35/10* | (2006.01) |
| *B01J 37/00* | (2006.01) |
| *B01J 37/02* | (2006.01) |
| *C10G 11/18* | (2006.01) |

(52) U.S. Cl.
CPC ............ *B01J 21/16* (2013.01); *B01J 21/185* (2013.01); *B01J 23/78* (2013.01); *B01J 35/1061* (2013.01); *B01J 37/0045* (2013.01); *B01J 37/0203* (2013.01); *B01J 37/04* (2013.01); *B01J 37/08* (2013.01); *C07C 5/3335* (2013.01); *C10G 11/18* (2013.01); *C07C 2521/16* (2013.01)

(58) Field of Classification Search
CPC ........ B01J 21/06; B01J 23/78; B01J 35/1061; C10G 11/18
See application file for complete search history.

(56) References Cited

U.S. PATENT DOCUMENTS

| | | | |
|---|---|---|---|
| 4,847,225 A | 7/1989 | Lussier | |
| 5,135,641 A * | 8/1992 | Pecoraro ............... | C10G 11/04 208/106 |
| 5,965,474 A * | 10/1999 | Balko .................. | B01J 29/005 208/113 |
| 6,849,248 B2 * | 2/2005 | Corma Canos ........ | B01J 29/035 208/46 |
| 7,410,924 B2 * | 8/2008 | Corma Canos ......... | B01J 23/85 502/64 |
| 2003/0057133 A1 * | 3/2003 | Benazzi ................ | C10G 45/62 208/49 |
| 2005/0165267 A1 * | 7/2005 | Canos .................... | B01J 23/40 502/64 |
| 2010/0084312 A1 * | 4/2010 | Maesen .................. | B01J 21/16 208/59 |
| 2012/0088654 A1 | 4/2012 | Wang et al. | |
| 2013/0130888 A1 | 5/2013 | Thota et al. | |

FOREIGN PATENT DOCUMENTS

EP        1797952 A2    6/2007

* cited by examiner

*Primary Examiner* — Jun Li
(74) *Attorney, Agent, or Firm* — The Webb Law Firm

(57) ABSTRACT

The present invention relates to a catalytic cracking catalyst for RFCC process with maximized diesel yield which includes a clay matrix and an inorganic oxide, wherein pores with a diameter greater than 20 Å are controlled, to be greater than 80% by volume of the total pore count of the catalyst, and a method for the preparation thereof.

14 Claims, No Drawings

CATALYTIC CRACKING CATALYST FOR RFCC PROCESS WITH MAXIMIZED DIESEL YIELDS AND A METHOD FOR THE PREPARATION THEREOF

CROSS REFERENCE TO RELATED APPLICATION

This application claims priority to Korean Patent Application No. 10-2014-0062083 filed May 23, 2014, the disclosure of which is hereby incorporated in its entirety by reference.

TECHNICAL FIELD

The present invention relates to a catalytic cracking catalyst for RFCC process and a method for the preparation thereof. More specifically, the present invention relates to a catalytic cracking catalyst for RFCC process with maximized diesel yield which comprises a clay matrix and an inorganic oxide, wherein pores with diameter greater than 20 Å are controlled to be greater than 80% by volume of the total pore count of the catalyst, and a method for the preparation thereof.

BACKGROUND ART

The RFCC process is a process for producing LPG, gasoline, diesel, naphtha and the like by further conducting a catalytic cracking reaction on a heavy residual oil that remains after the fractionation of a crude oil. According to the RFCC process, LPG, gasoline, diesel and the like are repoduceed by re-cracking the heavy residual oil which itself does not contain fuel. Thus, these are referred to as a ground oilfield and applied to an important advanced equipment of refinery companies.

Products which can be obtained through the RFCC process, include various substances based on the boiling point, such as LPG, gasoline and diesel, but the main target product to date is gasoline. In the current RFCC process, the yield of gasoline is approximately 50% by weight. Further, considering the MTBE and alkylate resulting from the C4 product obtained in the RFCC process, the yield of gasoline is in realty more than 60% by weight.

However, as the demand for gasoline is decreasing and shale-gas based gasoline alternative energy sources are developed, gasoline prices are falling continuously, and this trend is expected to be more extreme in the future.

In this regard, there is a need to change the target product of the RFCC process to substances other than gasoline. The substance which can be the most practical alternative can be seen as diesel.

On the other hand, the catalyst for conventional RFCC processes has been classified as a zeolite and a matrix, and the matrix was composed mainnly of kaolin clay. The zeolite and matrix have functions different from each other in the catalyst. If a petroleum feedstock containing a heavy residual oil is used, the cracking reaction occurs primarily a matrix having mesopores or macropores. Thus, through the primary cracking reaction, the petroleum feedstock, which has become small enough to enter the micropores of the zeolite, enters the zeolite micropores, the cracking reaction proceeds and the heavy residual oil is converted to LPG, gasoline and the like.

In other words, in the matrix, diesel (LCO, HCN) and heavy gasoline (HCN) are selectively produced through the pre-cracking of the heavy residual oil. In the zeolite, some LPG, light gasoline (LLCN, LCN) are selectively produced.

Depending on the components of the catalyst, the cracking functions of the catalysts are different from each other and so the components of the catalyst can be properly selected, thus controling the cracking performance. In other words, in order to obtain diesel, for which demand is recently increasing, the diesel yield can be maximized by not introducing zeolite into the catalytic cracking catalyst.

However, the catalytic cracking catalyst composed of only the matrix without introducing zeolite has two problems as follows:

First, the coke yield is lowered. Zeolite produces a catalytic coke while producing gasoline, LPG and the like in the RFCC process. Accordingly, if zeolite is not present in the catalyst, the generation of catalytic coke is reduced and the overall coke yield is lowered. The RFCC process maintains the heat balance through the coke. Therefore, if the coke yield is lowered, it may lead to a problem that the operation cannot be substantially performed.

Second, the cracking function is decreased due to external acid sites in zeolite. Since zeolites are materials having micropores, gasoline, LPG and the like can be selectively produced, but in addition there exists a pre-cracking function due to the external acid sites in zeolite. Accordingly, if zeolite is not present in the catalyst, the cracking function due to the external acid sites cannot be expected. There is a problem that the cracking performance generally falls.

DISCLOSURE OF INVENTION

Technical Problem

In view of the above described problems and recent changes in demand, the present invention provides a catalytic cracking catalyst for RFCC process for maximizing a diesel yield and a method for the preparation thereof. More specifically, the present invention provides a catalytic cracking catalyst for RFCC process with maximized diesel yield which comprises a clay matrix and an inorganic oxide, wherein pores with a diameter greater than 20 Å are controlled to be greater than 80% by volume of the total pore count the catalyst, and a method for the preparation thereof.

However, the technical problem to be solved by the present invention is not limited to the above, and other problems that are not mentioned herein will be clearly understood by those skilled in the art from the following description.

Technical Solution to the Problem

According to one embodiment of the present invention, a catalytic cracking catalyst for RECC process with maximized diesel yield which comprises a clay matrix and an inorganic oxide, wherein pores with a diameter greater than 20 Å are controlled to be greater than 80% by volume of the total pore count of the catalyst, is provided.

According to another embodiment of the present invention, a method for the preparation of a catalytic cracking catalyst for RFCC process with maximized diesel yield which comprises (a) step of mixing and stirring a clay and an inorganic oxide precursor to prepare a mixed slurry, and (b) a step of spray-drying the mixed slurry and then firing it, wherein the catalytic cracking catalyst prepared in the above steps has pores in which those with a diameter greater than 20 Å are controlled to be greater than 80% by volume of the total pore count of the catalyst, is provided.

Advantageous Effects

According to the catalytic cracking catalyst for RFCC process of the present invention, the following effects are avaialble.

First, when the catalytic cracking catalyst is applied to the RFCC process, the selectivity and yield of diesel can be maximized.

Second, the coke level can be maintained at a constant level by introducing metals of nickel or cobalt. Therefore, without changing the operating conditions, the cracking performance can be excellent.

Third, by introducing the slurry oil and firing it, the phenomenon in which the pre-cracking performance is reduced due to the absence of zeolite can be compensated for. Thus, the mesopores or macropores having various sizes in the catalyst are well-developed and the cracking performance is excellent.

Fourth, by introducing the metals of nickel or cobalt, the present invention can be used in the preparation of olefins through the RFCC process as well as the partial dehydrogenation reactions of paraffins.

Fifth, the catalytic cracking catalyst of the present inventon can more efficiently form carbon nanotubes on the surface or inside of the catalyst after the RFCC process, thus increasing the the production yield of carbon nanotubes.

BEST MODE

Hereinafter, the present invention is described in detail by way of embodiments of the invention such that it can be easily performed by those having ordinary skill in the art to which this invention belongs. The present invention may be embodied in several different forms, but should not be construed to be limited to the embodiments set forth herein.

Now, the present invention will be described in detail.

Catalytic Cracking Catalyst for RFCC Process

The present invention provides a catalytic cracking catalyst for RFCC process with maximized diesel yield which comprises a clay matrix and an inorganic oxide, wherein pores with a diameter greater than 20 Å are controlled to be greater than 80% by volume of the total pore count of the catalyst.

In order to maximize the diesel yield, the present invention provides a catalytic cracking catalyst which comprises a clay matrix and an inorganic oxide, without including zeolite.

Zeolite has pores with a diameter of 20 Å or less. Therefore, if zeolite is present in the catalytic cracking catalyst, the yield of compounds with a low carbon number and a small size such as gasoline or LPG is increased, and so the diesel yield is reduced. Accordingly, the catalytic crack-catalyst of the present invention is characterized in that the content of zeolite is very low regardless of whether any amount of zeolite is contained or not in the catalyst.

That is, the catalytic cracking catalyst of the present invention is characterized in maximzing the diesel yield by controlling pores with a diameter greater than 20 Å to be greater than 80% by volume of the total pore count of the catalyst.

The catalytic cracking catalyst of the present invention comprises a clay matrix. The kind of the clay may be kaolin, but is not limited thereto.

The above clay plays a role in controlling the physical properties such as the wear strength of the catalystic cracking catalyst. The pores contained in the clay matrix correspond to mesopores with a diameter of 30-40 Å and macropores with a dimameter of 50-60 Å, and play a role of increasing the yield of compounds having a higher carbon number relative to gasoline or diesel.

The clay may be used in the range from 80 to 95% by weight based on the total weight of the catalyic cracking catalyst of the present invention. When the content of the clay is less than 80% by weight, it is likely that the pre-cracking activity of the catalyst is low. When the content of the clay is more than 95% by weight, there may be a possibility of a problem with the catalyst strength due to the lack of binding material.

More preferably, the catalytic cracking catalyst of the present invention may be a catalyst in which the surface area of pores corresponding to a diameter of 20-150 Å is more than 70% of the total surface area.

In other words, because the clay constituting the matrix has a single pore structure due to the layer structure, there is a need to vary the pore structure of the matrix in order to improve the cracking performance of the petroleum feedstock containing various sizes of compounds. This is becasue only the hydrocarbon suitable for the pore structure can enter inside the pores and participate in the cracking reaction. The cracking is possible even at the external acid site of the matrix, but the pore structure depends on the surface area of the catalyst. Therefore, the pre-cracking due to the external acid sites in the matrix is very limited.

Accordingly, the catalytic cracking catalyst of the present invention further contains a slurry oil (SLO) having substantially the same size as the heavy oil feedstock during the preparation thereof, thereby forming pores corresponding to the size of slurry oil due to firing, and further the pre-cracking performance can be improved by controlling the degree of dispersion of the concerned pores.

Accordingly, the catalytic cracking catalyst of the present invention contains a slurry oil during one preparation thereof, and so the characteristic of the prepared catalyst is that the surface area of pores corresponding to a diameter of 20-150 Å may be more than 70% of the total surface area.

Herein, the content of the slurry oil in the catalytic cracking catalyst of the present invention may be determined from the viewpoint of maximizing the pre-cracking performance. That is, the pre-cracking performance of the catalytic cracking catalyst of the present invention may vary denpending on the properties of petroleum feedstocks such as API, naththenic content, and the properties of the catalyst such as the specific surface area of the clay matrix or the distribution of pores. Accordingly, the content of the slurry oil can be properly adjusted by those skilled in the art.

The catalytic cracking catalyst of the present invention can further comprise one or more selected among metals consisting of nickel and cobalt.

Because the catalytic cracking catalyst of the present invention does not contain zeolite or the content thereof is low, it is difficult to maintain the coke level at a constant level. Generally, because nickel and cobalt induce a dehydrogenation reaction in the RFCC process to generate coke and $H_2$, a conventional catalytic cracking catalyst preferably inhibits the inclusion of the nickel and cobalt in the catalytic cracking catalyst.

However, because the catalytic cracking catalyst of the present invention does not contain zeolite or its content is low, it may further comprise one or more selected among the metals consiting of cobalt and nickel, thereby increasing the coke yield. Therefore, the catalytic cracking catalyst may include nickel and cobalt.

In this case, the metal content of nickel or cobalt in the catalytic cracking catalyst of the present invention can be determined from the viewpoint of maintaining the coke level at the appropriate level. That is, the coke level of the catalytic cracking catalyst of the present invention may vary depending on the properties of petroleum feedstocks such as API, naththenic content, and the properties of the catalyst such as the distribution of pores. Accordingly, the content of the nickel or covalt can be properly adjusted by those skilled in the art.

The inorganic oxide contained in the catalytic cracking catalyst of the present invention can be $Al_2O_3$, $SiO_2$, $AlO(OH)$, or $Al_2O_3$-$SiO_2$. The inorganic oxide serves as a binder for producing the catalyst. At the time of manufacture, a precursor in the form of sol, gel or solution containing $Al_2O_3$, $SiO_2$, $AlO(OH)$, or $Al_2O_3$-$SiO_2$ is used.

The content of the inorganic oxide binder in the catalytic cracking catalyst of the present invention may range from 5 to 25% by weight based on the total weight of the catalyst. If the amount of the inorganic oxide is less than 5% by weight, there is a problem in that the abrasion strength of the catalyst is weak. If the amount of the inorganic oxide exceeds 25% by weight, there is a problem in that the catalytic cracking activity decreases.

Meanwhile, the catalytic cracking catalyst of the present invention can be utilized for the production of olefins via the RFCC process as well as the partial dehydrogenation reactions of paraffins by introducing the metals of nickel or cobalt.

The partial dehydrogenation reaction refers to an olefin production reaction through the dehydrogenation reaction of paraffins. In general, the partial dehydrogenation reaction uses a catalyst in the form of a metal/support. The metals may be the metals having hydrogenation/dehydrogenation activity and corresponding to from the 8B group to 5B group in the periodic table, and further, metals of the 1B group containing Cu and alloys thereof can be used. As the support, alumina is frequently applied, but various carriers such as carbon, silica or silica-alumina can be applied. The catalytic reaction can be applied in various reactors including a continuous flow reactor, or a fluidized bed reactor. The reaction temperature varies depending on the catalyst, but the reacton is perfomed preferably at a temperature of 150 to 500° C.

The catalytic cracking catalyst of the present invention can be applied to the above-mentioned partial dehydrogenation reaction. In this case, the content of the supported Ni is preferably 5 to 10% by weight. If the supported metal is Co, the content is preferably 10 to 30% by weight. If the content is less than 5% by weight based on the content of Ni, the partial dehydrogenation activity is relatively lowered. If it exceeds 10% by weight, it is likely that the economic efficiency is lowered due to an increase in the coke yield according to an increase in the olefin yield. The same applies for supported meals using Co.

Also, the catalytic cracking catalyst of the present invention can more efficiently form carbon nanotubes on the surface or inside thereof after the RFCC process, thus improving the production yield of carbon nanotubes.

The initial coke formed from Ni, Co, Fe and the like of conventional RFCC E-cat. is a carbon nanotube, and it is possible to produce a certain amount of carbon nanotubes through the conventional RFCC E-cat. by introducing a light olefin as a raw material in the RFCC catalyst reaction.

However, in the case of the conventional RFCC E-cat., the metal content is low in the level of 1% by weight, and mesopores and macropores are well-developed. Therefore, if this process is applied to the production reaction of carbon nanotubes, the carbon nanotubes are not only generated in a small amount, but also there is a difficulty in recovering them. Therefore, the catalyst for producing carbon nanotubes is now in a form in which Fe is supported in the amount of about 3-10% by weight in the alumina support pores, in which the pores are barely developed, and it is used at reaction conditions of 350 to 600° C. in the fluidized bed reactor. Because of these limitations, the cost of the catalyst for the production of the carbon nanotubes is at a level which is not negligible in the production reaction of carbon nanotubes.

The catalytic cracking catalyst of the present invention has a metal content of Ni 5% by weight or more, and so is suitable for the production of carbon nanotubes. Under the same operating conditions as those of the conventional method, the catalytic cracking catalyst of the present invention inhibits producing the carbon nanotubes and then growing them into a large coke, and can obtain the production yield of carbon nanotubes at a certain level or more. The carbon nanotubes are produced on the surface and inside of the catalyst. Accordingly, the catalyst can be dissolved in HF and the like, filtered, recovered and easily separated.

Method for the Preparation of the Catalytic Cracking Catalyst for RFCC Process

The present invention provides a mehtod for preparation of a catalytic cracking catalyst for RFCC process with maximized diesel yield which comprises (a) a step of mixing and stirring a clay and an inorganic oxide precursor to prepare a mixed slurry, and (b) a step of spray-drying the mixed slurry and then firing it, wherein the catalytic cracking catalyst prepared in the above steps has pores in which those with a diameter greater than 20 Å are more than 80% by volume of the total pore count of the catalyst.

That is, the catalytic cracking catalyst for RFCC process according to the present invention is produced by mixing and stirring a clay and an inorganic oxide precursor to prepare a mixed slurry, spray-drying the mixed slurry and then firing it, wherein the cracking catalyst has pores in which those with a diameter greater than 20 Å are more than 80% by volume of the total pore count of the catalyst.

In another embodiment of the present invention, the catalytic cracking catalyst of the present invention as described above can be produced by further including nickel precursor or a cobalt precursor when preparing the mixed slurry in the step (a). The effect generated by further including the nickel or cobalt precursors is as described above.

In a futher embodiment of the present invention, the catalytic cracking catalyst of the present invention as described above can be produced by further including a slurry oil during the production of the mixed slurry in step (a). The effect generated by further comprising the slurry oil is as described above.

The catalytic cracking catalyst in accordance with the present invention is prepared by spray-drying the mixed slurry and then firing it at 500-700° C. for 5-10 hours.

Hereinafter, the consitution and method for achieving the object of the present invention is described in more detail by way of examples. However, it is not intended that the scope of the invention be limited to these examples.

EXAMPLE 1

(1) Preparation of Catalyst 398 g of kaolin clay and 3.0 g of MgO were mixed well and stirred to prepare mixture. Meanwhile, 157 g of PEA (Pseudoboehmite alumina), 110 g of DI-water and 43 g of Ludox (AS 40) were mixed in a beaker in which 15. 7 g of formic acid was introduced. The viscosity of the mixture was then confirmed with slowly stirring. When the viscosity increased gradually and changed from a sol state to a gel state, the above prepared mixture of kaolin clay and MgO was poured, and again stirred at 6,000 rpm for 10 minutes. When it came to a suitable viscosity to be introduced into a spray drier, it was introduced into a spray drier to produce a RFCC forming catalyst. The prepared catalyst was fitted to have a diameter of 20~180 um and used. The yield of the selected catalyst was 90% or more. The catalyst was fired at 550° C. for 3 hours while flowing air under the conditions of 100 sccm, The prepared catalyst had pores in which those with a diameter greater than 20 Å were 90% by volume of the total pore count of the catalyst.

(2) Deactivation of Catalyst

In order to evaluate the activity of the RFCC catalyst as prepared above, a fresh catalyst of the RFCC process was subjected to XRD analysis of D-cat. under various CPS operation conditions. The results confirmed that the most similar catalytic activity to E-cat. was obtained under CPS30 cycle operating conditions. The catalytic cracking catalyst produced in the above (1) under CPS30 cycle operating conditions was deactivated.

More specifically, in 1 kg or the catalytic cracking catalyst produced in the above (1), Ni, V and Fe were introduced at 3000, 4000, and 3000 ppm, respectively. Ni, V and Fe were introduced by the method wherein the compound precursors in the form of naphthenate were dissolved in toluene, supported on the prepared catalyst and dried. By repeating these methods, the cracking catalyst was produced in a total amount of 4 kg 4 kg of the catalytic cracking catalyst in which Ni, V, Fe were introduced in 3000, 4000, and 3000 ppm, respectively, was introduced into the CPS equipment. Water/catalyst was operated under 0.04 h-1 conditions, 1 cycle was configured to maintain for 10 minutes each step at 788° C. under the conditions of $N_2$, air, $N_2$, 5% propylene ($N_2$ balance). This was driven for 30 cycles, and finally deactivated catalytic cracking catalyst was produced.

(3) Confirmation of the Cracking Performance 2 kg of the catalytic cracking catalyst of the present invention deactivated in the above (2) confirmed the cracking performance through DCR pilot test. The physical properties of the petroleum feedstock used is shown in Table below.

TABLE 1

| Item | Unit | Analytical value |
|---|---|---|
| API | 60° F. | 21.1 |
| Sulfur | Wt. % | 0.41 |
| Nitrogen | Mg/kg | 1023 |
| MCRT | Wt. % | 3.77 |
| Asphaltenes | Wt. % | 0.3 |
| Fe | Mg/kg | 4.9 |
| Ni | Mg/kg | 3.3 |
| V | Mg/kg | 3.9 |

TABLE 1-continued

| Item | Unit | Analytical value |
|---|---|---|
| D1160(° C.) | IBP | 292.9 |
|  | 5% | 378.2 |
|  | 10% | 399.1 |
|  | 30% | 458.3 |
|  | 50% | 512.5 |
|  | 60% | 544.2 |
| Recovery | Vol. % | 66 |

The petroleum feedstock was introduced into the reactor under a condition of 500 g/h, and the stream of the reactor was introduced under a condition of 90 g/h. The reactor was operated at a temperature of 562° C. and the regenerator was operated at a temperature of 700° C. The overall reaction pressure was 1.6 kgf/cm$^2$ g. After completion of the reaction, the resulting gas product was analyzed by GC-RGA, and the liquid product was analyzed by GC-simdist. The coke analysis was performed using the CO/CO$^2$ analyzer.

EXAMPLE 2

(1) Preparation of Catalyst 398 g of kaolin clay and 3.0 g of MgO were mixed well in which 15.0 g of a slurry oil remained after the decomposition in the RFCC process was introduced. Meanwhile, 157 g of PBA (Pseudoboehmite alumina), 110 g of DI-water and 43 g of Ludox (AS 40) were mixed in a beaker in which 15.7 g of formic acid was introduced. The viscosity of the mixture was confirmed with slowly stirring. When the viscosity increased gradually and changed from a sol state to a gel state, the above prepared mixture of kaolin clay and MgO was poured, and again stirred at 6, 000 rpm for 10 minutes. When it has come to a suitable viscosity to be introduced into a spray drier, it was introduced into a spray drier to produce a RFCC forming catalyst. When the viscosity of the slurry was not suitable, DI-water was added and the viscosity was suitably adjusted to introduce in the spray-dryer. The prepared catalyst was fitted to have a diameter of 20~180 um and used. The yield of the selected catalyst was 90% or more. The catalyst was fired at 550° C. for 3 hours while flowing air under the conditions of 100 sccm, The prepared catalyst had pores in which those with a diameter greater than 20 Å were 92% by volume of the total pore count of the catalyst,

(2) Deactivation of the Catalyst and Confirmation of the Cracking Performance The catalyst was deactivated under the same conditions as Example 1, and then operated under the same DCR operation conditions except that the reaction temperature was 567° C., to confirm the cracking performance.

EXAMPLE 3

(1) Preparation of Catalyst

The catalyst in which 3% by weight of nickel was introduced was prepared by dissolving nickel naphthenate in toluene and then supporting it on the catalyst obtained in Example 1.

(2) Deactivation of the Catalyst and Confirmation of the Cracking Performance The catalyst was deactivated under the same conditions as Example 1, and then operated under the same DCR operation conditions except that the reaction temperatujre was 554° C., to confirm the cracking performance.

EXAMPLE 4

(1) Preparation of Catalyst

The catalyst in which 5% by weight of cobalt was introduced was prepared by dissolving cobalt naphthenate in toluene and then supporting it on the catalyst obtained in Example 1.

(2) Deactivation of the Catalyst and Confirmation of the Cracking Performance

The catalyst was deactivated under the same conditions as Example 1, and then operated under the same DCR operation conditions except that the reaction temperature was 557° C., to confirm the cracking performance.

EXAMPLE 5

(1) Preparation of Catalyst

The catalyst in which 3% by weight of nickel was in was prepared by dissolving nickel naphthenate in toluene and then supporting it on the catalyst obtained in Example 2.

(2) Deactivation of the Catalyst and Confirmation of the Cracking Performance

The catalyst was deactivated under the same conditions as Example 1, and then operated the same DCR operation conditions except that the reaction temperatujre was 557° C., to confirm the cracking performance.

EXAMPLE 6

(1) Preparation of Catalyst

The catalyst in which 5% by weight of cobalt was introduced was prepared dissolving cobalt naphthenate in toluene and then supporting it on the catalyst obtained in Example 2.

(2) Deactivation of the Catalyst and Confirmation of the Cracking Performance

The catalyst was deactivated under the same conditions as Example 1, and then operated under the same DCR operation conditions except that the reaction temperatujre was 559° C., to confirm the cracking performance.

COMPARATIVE EXAMPLE (1) Catalyst

In order to confirm the physical properites of 800 g of E-Cat. generated in the RFCC process, the catalyst was subjected to BET, XRD and XRF analysis and then the presence and content of zeolite in the catalyst were confirmed. The content of zeolite in the catalyst was 20.5% by weight and this was calculated based on the specific surface area of the zeolite surface zone. The ratio (Z/M) of a specific surface area of zeolite and a specific surface area of matrix was 0.4, based on the specific surface area.

(2) Application to the RFCC Process

The heavy residual oil as the petroleum feedstock was catalytically reacted with the above prepared catalyst in a reaction zone of a fluidized bed catalytic cracking unit to thereby obtain a product stream, an unreacted petroleum feedstock and a mixture of the used catalysts. The product stream was separated and collected from the used catalyst and the unreacted petroleum feedstock.

Evaluation

With respect to the product stream obtained in the RFCC process of the Examples and Comparative Examples, the selectivity and content of diesel, gasoline and $H_2$ were evaluated and the results are shown in Table 2 below.

TABLE 2

| | Diesel | Gasoline | $H_2$ | Gas product | Slurry oil | Coke |
|---|---|---|---|---|---|---|
| Example 1 | 31.95 | 29.91 | 0.19 | 23.42 | 6.62 | 7.91 |
| Example 2 | 33.27 | 27.12 | 0.18 | 25.19 | 6.31 | 7.93 |
| Example 3 | 35.41 | 32.89 | 0.85 | 15.7 | 7.23 | 7.92 |
| Example 4 | 33.7 | 32.03 | 0.67 | 18.61 | 7.09 | 7.9 |
| Example 5 | 39.04 | 29.16 | 0.88 | 16.14 | 6.85 | 7.93 |
| Example 6 | 36.47 | 30.81 | 0.74 | 17.35 | 6.71 | 7.92 |
| Comparative Example 1 | 16.59 | 48.18 | 0.24 | 19.34 | 7.72 | 7.93 |

Diesel had the temperature ranging from 200 to 360° C., and gasoline was defined as a liquid product of not greater than 200° C. The gas product is a product corresponding to C1-C4, and the slurry oil is an unreacted slurry oil. The comparison was performed by an iso-coke criteria which is an operation criteria actually available in commercial plants. The iso-coke comparison was performed at at coke yield of 7.93%.

As can be seen from Table 2, wing the catalytic cracking catalyst of the present invention, the selectivity and yield of diesel were significantly increased an the selectivity and yield of gasoline were lowered.

Moreover, it could be seen that, by further introducing metals of nickel or cobalt into the catalyst, the yield of $H_2$ was high.

The foregoing description of the present invention is for purposes of illustration, and it will be very apparent to one of ordinary skill in the art that modifications can be easily made in other specific forms without changing the technical spirit or essential feature of the present invention. Therefore, the embodiments described above are intended to be illustrative in all respects and should be understood to not be limiting.

What is claimed is:

1. A catalytic cracking catalyst for a residue fluid catalytic cracking (RFCC) process which comprises a clay matrix, and an inorganic oxide, wherein pores with a diameter greater than 20 Å are more than 80% by volume of the total pore count of the catalyst,
   wherein the catalytic cracking catalyst comprises nickel, wherein the content of the nickel is 5 to 10% by weight, and wherein the catalytic cracking catalyst does not include zeolite.

2. The catalytic cracking catalyst for RFCC process according to claim 1 wherein the catalytic cracking catalyst is a catalyst in which the surface area of pores corresponding to a diameter of 20-150 Å is more than 70% of the total surface area.

3. The catalytic cracking catalyst for RFCC process according to claim 1 wherein the inorganic oxide is $Al_2O_3$, $SiO_2$, $AlO(OH)$, or $Al_2O_3$-$SiO_2$.

4. The catalytic cracking catalyst for RFCC process according to claim 1 wherein the catalytic cracking catalyst is used for the partial dehydrogenation reaction.

5. The catalytic cracking catalyst for RFCC process according to claim 1 wherein the catalytic cracking catalyst forms carbon nanotubes on the surface or inside thereof after the RFCC process.

6. A catalytic cracking catalyst for a residue fluid catalytic cracking (RFCC) process which comprises a clay matrix, and an inorganic oxide, wherein pores with a diameter greater than 20 Å are more than 80% by volume of the total pore count of the catalyst, wherein the catalytic cracking catalyst comprises cobalt, wherein the content of the cobalt is 10 to 30% by weight, and wherein the catalytic cracking catalyst does not include zeolite.

7. The catalytic cracking catalyst for RFCC process according to claim 6 wherein the catalytic cracking catalyst is a catalyst in which the surface area of pores corresponding to a diameter of 20-150 Å is more than 70% of the total surface area.

8. The catalytic cracking catalyst for RFCC process according to claim 6 wherein the inorganic oxide is $Al_2O_3$, $SiO_2$, AlO(OH), or $Al_2O_3$-$SiO_2$.

9. The catalytic cracking catalyst for RFCC process according to claim 6 wherein the catalytic cracking catalyst is used for the partial dehydrogenation reaction.

10. The catalytic cracking catalyst for RFCC process according to claim 6 wherein the catalytic cracking catalyst forms carbon nanotubes on the surface or inside thereof after the RFCC process.

11. A method for the preparation of a catalytic cracking catalyst for a residue fluid catalytic cracking (RFCC) process comprising:
   (a) a step of mixing and stirring a clay and an inorganic oxide precursor to prepare a mixed slurry, and
   (b) a step of spray-drying the mixed slurry and then firing it,
   wherein the catalytic cracking catalyst prepared in the above steps has pores in which those with a diameter greater than 20 Å are more than 80% by volume of the total pore count of the catalyst wherein the catalytic cracking catalyst comprises 5-10% by weight of nickel or 10-30% by weight of cobalt, and
   wherein the catalytic cracking catalyst does not include zeolite.

12. The method for the preparation of a catalytic cracking catalyst for RFCC process according to claim 11, wherein the catalytic cracking catalyst is a catalyst in which the surface area of pores corresponding to a diameter of 20-150 Å is more than 70% of the total surface area.

13. The method for the preparation of a catalytic cracking catalyst for RFCC process according to claim 11, further comprising a nickel precursor or a cobalt precursor during the preparation of the mixed slurry in the step (a).

14. The method for the preparation of a catalytic cracking catalyst for RFCC process according to claim 11, further comprising a slurry oil during the production of the mixed slurry in step (a).

* * * * *